United States Patent [19]

Hardy

[11] Patent Number: 5,195,974
[45] Date of Patent: Mar. 23, 1993

[54] NEEDLE PROTECTOR FOR A CATHETER ASSEMBLY

[75] Inventor: Dwayne E. Hardy, San Mateo, Calif.

[73] Assignee: Menlo Care, Inc., Menlo Park, Calif.

[21] Appl. No.: 115,158

[22] Filed: Oct. 30, 1987

[51] Int. Cl.$^5$ ............................................. A61M 5/00
[52] U.S. Cl. .................................. 604/110; 604/164; 604/263
[58] Field of Search ........................... 604/158–169, 604/198, 110, 263, 192; 128/763, 766; 206/364, 365

[56] References Cited

U.S. PATENT DOCUMENTS

| | | | |
|---|---|---|---|
| 3,438,373 | 4/1969 | Pannier | 604/159 |
| 3,592,192 | 7/1971 | Harautuneian | 604/165 |
| 3,875,938 | 4/1975 | Mellor | 604/164 |
| 4,160,450 | 7/1979 | Doherty | 604/164 |
| 4,177,809 | 12/1979 | Moorehead | 604/164 |
| 4,676,783 | 6/1987 | Jagger et al. | 604/162 X |
| 4,681,567 | 7/1987 | Masters | 604/198 |
| 4,695,274 | 9/1987 | Fox | 604/263 X |
| 4,725,267 | 2/1988 | Vaillancourt | 604/263 X |
| 4,747,831 | 5/1988 | Kulli | 604/110 |

FOREIGN PATENT DOCUMENTS 0227230 1/1987 European Pat. Off. .
0233055 8/1987 European Pat. Off. .

OTHER PUBLICATIONS

Hanley, "ICU 'High Risk' Needle Protects Health Workers", L.A. Times, Nov. 13, 1986.

*Primary Examiner*—John D. Yasko
*Assistant Examiner*—Anthony Gutowski
*Attorney, Agent, or Firm*—Fliesler, Dubb, Meyer & Lovejoy

[57] ABSTRACT

An improved catheter assembly is set forth having a cannula having a proximal and distal end portions and longitudinal duct therethrough from said proximal to said distal end portion. A longitudinal piercing member having a distal end having a sharp insertion tip is positioned within the longitudinal duct of the cannula with the insertion tip extending beyond the distal end portion of the cannula. A hub having a passageway therethrough from its proximal to its distal end thereof has its distal end attached to the proximal end portion of the cannula with the passageway in flow communication with the duct in the cannula. A longitudinal piercing member extractor construction extends longitudinally from the longitudinal piercing member. The extractor construction extends through the duct of the cannula and through the passageway of the hub to a proximal end of the extractor construction. The improvement of the invention comprises a rigid longitudinal piercing member receiving tube having proximal and distal end portions and a longitudinal bore therethrough from the proximal to the distal end portion, the tube being adjacent to the proximal end of the hub, the extractor construction extending from the passageway through and beyond the bore of the tube. A structure is provided which retains the longitudinal piercing member such that its sharp insertion tip is enclosed in the receiving tube. A needle or stylet which is removed by an extractor construction has its sharp insertion tip entrapped within the receiving tube thereby protecting attending medical personnel from being accidentally stuck thereby. The chances of spread of communicable diseases such as AIDS is thereby significantly reduced.

12 Claims, 3 Drawing Sheets

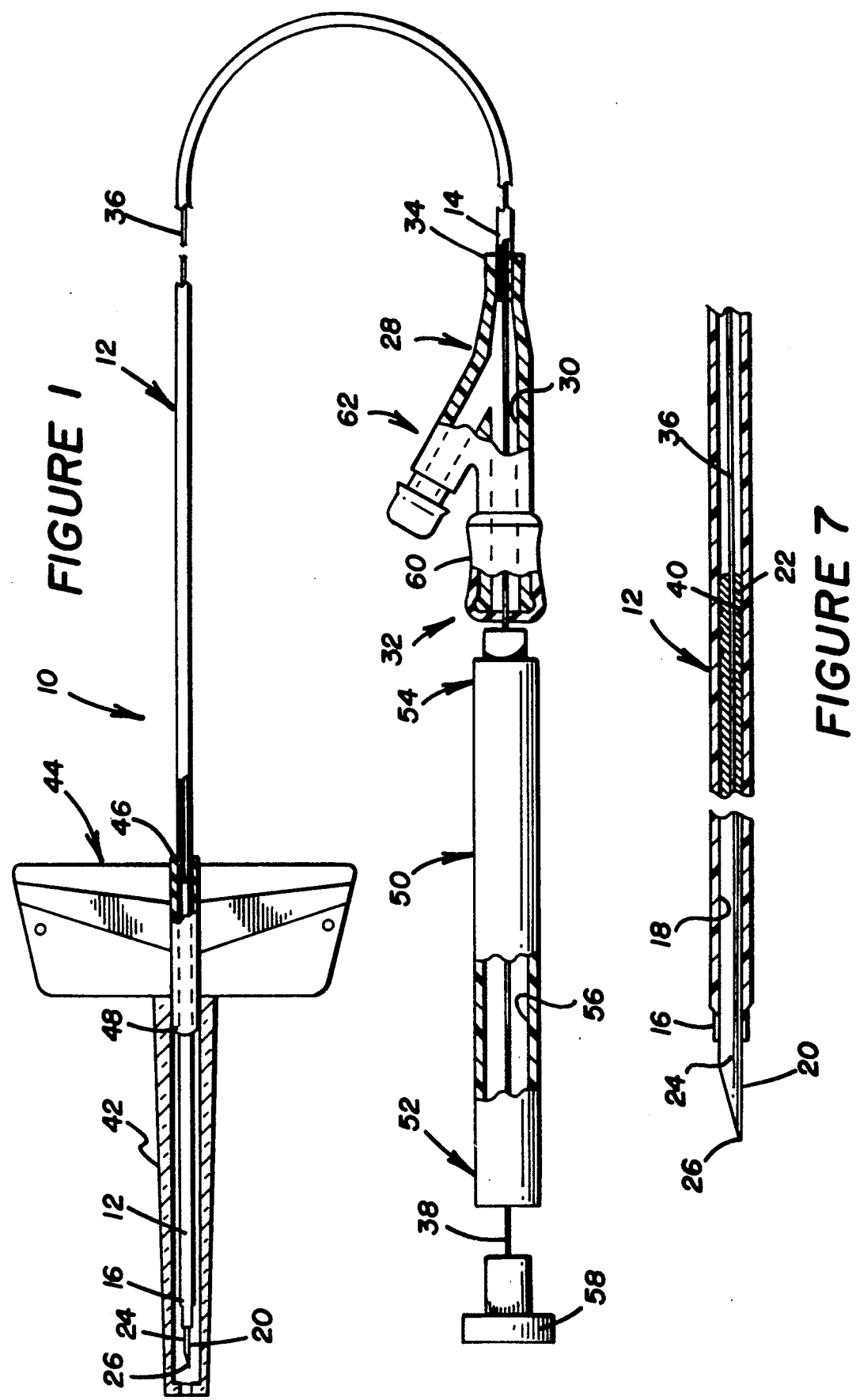

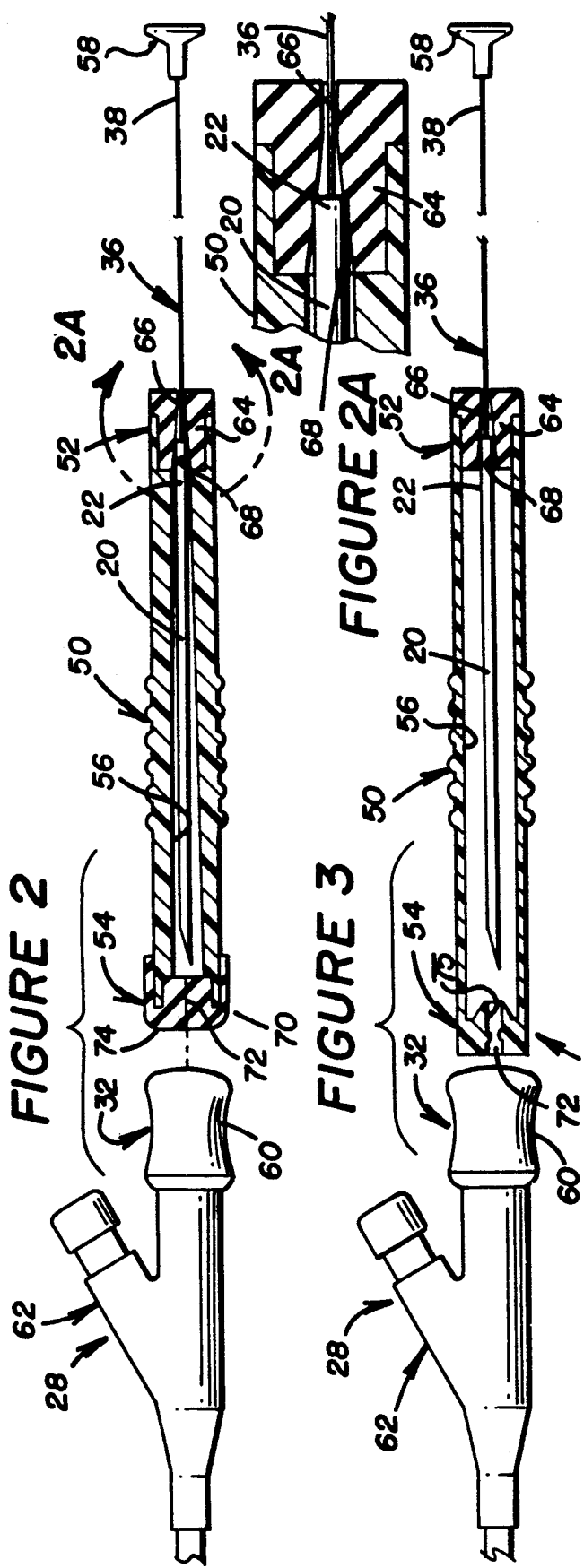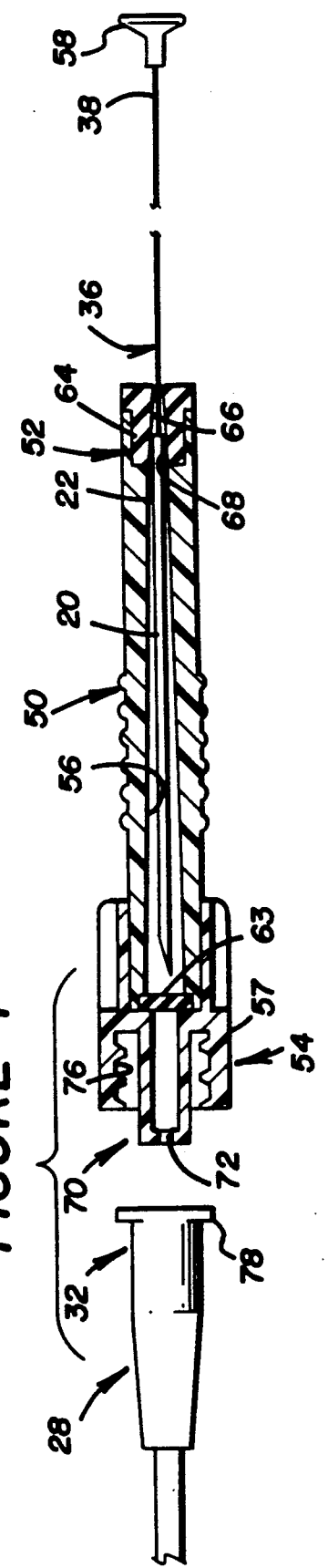

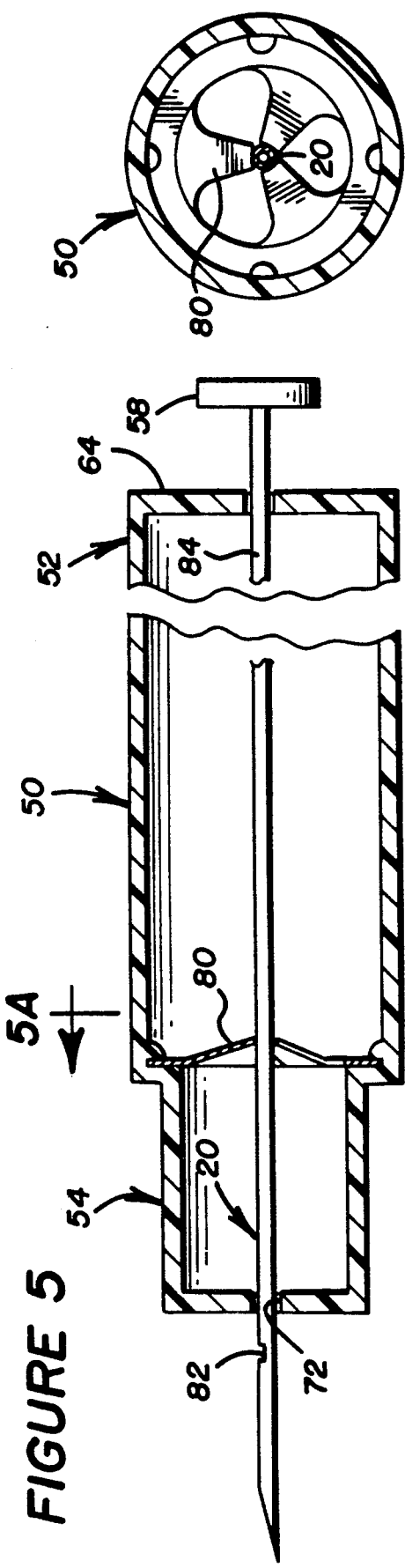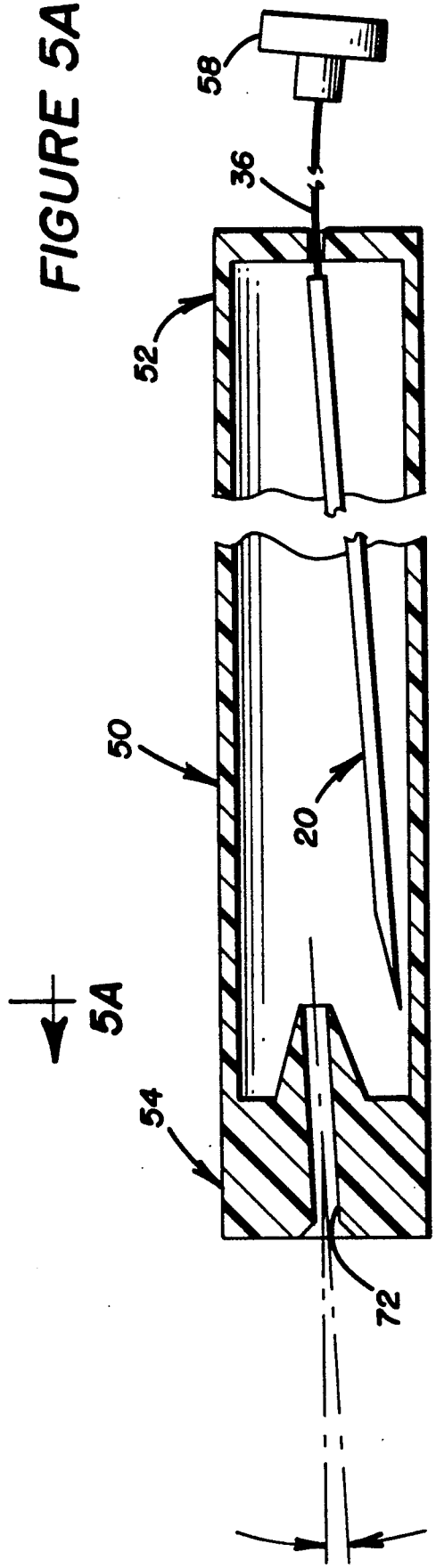

NEEDLE PROTECTOR FOR A CATHETER ASSEMBLY

FIELD OF THE INVENTION

The invention relates to a protector for a needle or stylet which is withdrawn from a catheter assembly by means of an extractor wire. More particular, the invention relates to a protector for such a stylet or needle which is used to insert a cannula in the blood stream with the cannula located radially about the stylet or needle.

BACKGROUND OF THE INVENTION

A number of catheter assemblies are known for the introduction of a polymeric cannula into a vein, artery or body cavity of a living subject for infusion or extraction of fluids.

In one apparatus, a steel needle or stylet (hereafter referred to as needle, for convenience) is sized to fit within the duct of the cannula and the piercing tip of the needle exits its distal end. The needle is inserted into the living subject after which the needle is removed from the cannula, leaving the cannula behind with at least its distal end in the subject. Additional tubing can be attached thereto or medicaments or nutrients can be caused to flow through the cannula into the subject. Also, the cannula can be relatively long and can be fed into the vein, artery or body cavity through an appropriate catheter holder which can itself be attached to the body adjacent the point of entry of the cannula through the skin. The needle is removed by having an extractor, which may be an extraction wire or a continuation of the needle, extending longitudinally from its proximal end. The extractor can pass through any additional length of the cannula and also passes through the hub which holds the cannula and out the proximal end of the hub.

A problem which exists with such a catheter assembly is that when the extractor is used to pull the needle or stylet through the cannula and then through the hub, one ends up with a sharp instrument exposed, namely the needle or stylus, which may be infected with virulent bacteria, virus and the like. In such instances hospital personnel can inadvertently stab themselves with the needle or stylet, even if the personnel are wearing rubber gloves, and thereby contact an infectious disease, such as AIDS, hepatitis, or the like.

Several needle encasing or protecting apparatus have been designed to prevent hospital personnel from being accidently stabbed by the needles of conventional barrel and plunger hypodermic syringes where such needles are not utilized to position a cannula and where such needles do not have an extraction wire attached to them and are not pulled through the cannula prior to being discarded. For example, U.S. Pat. No. 4,643,199, issued Feb. 17, 1987 to B. P. Jennings, Jr. and P. M. Kivlighan, U.S. Pat. No. 4,650,468, issued Mar. 17, 1987 to B. P. Jennings, Jr., U.S. Pat. No. 4,675,005, issued Jun. 23, 1987 to J. DeLuccia and U.S. Pat. No. 4,681,567, issued Jul. 21, 1987 to E. J. Masters and P. L. Ebaugh each show a the needle being withdrawn into the barrel of a conventional hypodermic syringe.

U.S. Pat. No. 4,676,783, issued Jun. 30, 1987 to J. C. Jagger, R. D. Pearson and P. C. Guyenet relates to a needle assembly wherein a needle is withdrawable into a cylinder to which wings are attached for gripping. The proximal end of the needle is wedged in place thus holding the needle within the cylinder.

One apparatus, sold under the trademark "SafeSide" by LUMED, removes a needle from the inside of a cannula after the needle and cannula have been inserted in the blood vessel. The apparatus is in the nature of two relatively slidable tubes, one within the other. A hub is attached to the distal end of the inner tube, the hub carrying a plastic cannula extending longitudinally therefrom. The needle extends concentrically within the cannula and extends beyond the distal end of the cannula for piercing the skin and the blood vessel. Once the needle and cannula have been inserted in a blood vessel the outer tube is moved proximally relative to the inner tube whereby the needle is withdrawn from the cannula and ends up being positioned within the inner tube. Once the tubes have been pulled apart as far as is possible they lock into place so that the needle is kept covered.

None of the above described apparatus is, however, adaptable to receiving and protecting a needle or stylet which is withdrawn through a hub, for example, utilizing an extraction wire. Also, such an assembly is limited in that one cannot feed a desired length of catheter into the blood vessel but, instead, can only insert the length of catheter which originally covered the needle (from the skin line inwardly into the blood vessel).

The present invention is directed to overcoming one or more of the problems as set forth above.

DISCLOSURE OF THE INVENTION

In accordance with an embodiment of the present invention an improvement is set forth in a catheter assembly having a cannula having a proximal end portion, a distal end portion and a longitudinal duct therethrough from the proximal end portion to the distal end portion; a longitudinal piercing member having a distal end having a sharp insertion tip, the longitudinal piercing member being positioned within the longitudinal duct of the cannula with the insertion tip extending beyond the distal end of the cannula; a hub having a passageway therethrough from the proximal end to the distal end thereof, the proximal end portion of the cannula being attached adjacent the distal end of the hub with the passageway in flow communication with the duct in the proximal end portion of the cannula; and an extractor construction extending longitudinally from the longitudinal piercing member, the extractor construction extending through the duct of the cannula and through the passageway of the hub to a proximal end of the extractor construction. The improvement comprises a rigid longitudinal piercing member receiving tube having proximal and distal end portions and a longitudinal bore therethrough from its proximal to its distal end portion, the tube being adjacent to the proximal end of the hub, the extractor construction extending from the passageway through and beyond the bore of the tube. Means is provided for retaining the longitudinal piercing member such that its sharp insertion tip is enclosed in the tube.

In accordance with another embodiment of the present invention an improvement is set forth in a catheter assembly having a cannula having a proximal end portion, a distal end portion and a longitudinal duct therethrough from the proximal end portion to the distal end portion; a longitudinal piercing member having a proximal end and a distal end having a sharp insertion tip, the longitudinal piercing member being positioned within the longitudinal duct of the cannula with the insertion tip extending beyond the distal end of the cannula; a hub having a passageway therethrough from the proximal end to the distal end thereof, the proximal end portion of the cannula being attached adjacent the distal end of the hub with the passageway in flow communication with the duct in the proximal end portion of the cannula; and an extraction wire having proximal and distal ends, the wire being of smaller diameter than the needle, having the distal end thereof attached to extend longitudinally from the proximal end of the longitudinal piercing member, the extraction wire extending through the duct of the cannula and through the passageway of the hub to the proximal end of the wire. The improvement comprises a rigid longitudinal piercing member receiving tube having proximal and distal end portions and a longitudinal bore therethrough from its proximal to its distal end portion, the tube being adjacent to the proximal end of the hub, the extraction wire extending from the passageway through and beyond the bore of the tube. A first closure is across the proximal end portion of the tube, the closure having a generally central opening large enough to allow the wire to pass longitudinally therethrough but too small to allow the longitudinal piercing member to pass longitudinally fully therethrough. A second closure is located across a distal end portion of the tube, the second closure having a generally central access through which the wire and the longitudinal piercing member can longitudinally pass.

In accordance with the present invention a needle or stylet can be withdrawn from a cannula by pulling on a wire which is attached to extend from the proximal end of the needle or stylet and the needle or stylet is drawn into a rigid receiving tube which completely encloses it and protects health professionals from being accidentally stabbed with the needle or stylet thereby preventing direct body fluid contact which can lead to transmission of disease, particularly AIDS and/or hepatitis.

BRIEF DESCRIPTION OF DRAWINGS

The invention will be better understood by reference to the figures of the drawings wherein like numbers denote like parts throughout and wherein:

FIG. 1 illustrates, in side view, partially in section, a catheter assembly in accordance with an embodiment of the present invention;

FIG. 2 illustrates, in side view, partially in section, a needle or stylet receiving tube in accordance with an embodiment of the present invention;

FIG. 2A illustrates, in enlarged view, a detail in the embodiments of FIGS. 2, 3 and 4;

FIG. 3 illustrates, in a view similar to FIG. 2, an alternative embodiment of a needle or stylet receiving tube in accordance with an embodiment of the present invention;

FIG. 4 illustrates, in a view similar to FIG. 2, still another embodiment of a needle or stylet receiving tube in accordance with an embodiment of the present invention;

FIG. 5 illustrates, in a view similar to FIG. 2, another embodiment yet of a needle or stylet receiving tube in accordance with an embodiment of the present invention;

FIG. 5A is a view along line 5A—5A of FIG. 5;

FIG. 6 illustrates, in a view similar to FIG. 2, a further embodiment of a needle or stylet receiving tube in accordance with an embodiment of the present invention; and FIG. 7 illustrates, partially in section, a detail in the structure of an embodiment in accordance with the present invention.

BEST MODE FOR CARRYING OUT INVENTION

Referring first to FIGS. 1 and 7, a catheter assembly 10 is illustrated having a cannula 12 having a proximal end portion 14, a distal end portion 16 and a longitudinal duct 18 which passes through the cannula 12 from the proximal end portion 14 to the distal end portion 16. A longitudinal piercing member 20 (a needle or stylet) has a proximal end 22 and a distal end 24. The distal end 24 has a sharp insertion tip 26. The longitudinal piercing member 20 is positioned within the longitudinal duct 18 of the cannula 12 with the insertion tip 26 extending beyond the distal end portion 16 of the cannula 12.

A hub 28 has a passageway (FIG. 1) therethrough from the proximal end 32 thereof to the distal end 34 thereof. The proximal end portion 14 of the cannula 12 is attached adjacent the distal end 34 of the hub 28 with the passageway 30 in flow communication with the duct 18 in the proximal end portion 14 of the cannula 12. The proximal end portion of the cannula 12 can be attached, for example, by a simple force interference fit between the distal end 34 of the hub 28 and a metal sleeve or eyelet (not illustrated).

An extractor construction, for example an extraction wire 36, has a proximal end 38 and a distal end 40. The extraction wire 36 is of smaller diameter than is the longitudinal piercing member 20 and has its distal end 40 attached to extend longitudinally from the proximal end 22 of a longitudinal piercing member 20. This can be accomplished by simply crimping (see FIG. 7) the proximal end 22 of the longitudinal piercing member 20 (which in this instance is in the form of a needle) about the distal end 40 of the extraction wire 36. The extraction wire 36 extends through the duct 18 of the cannula 12 and through the passageway 30 of the hub 28 to the proximal end 38 of the extraction wire 36.

A removeable, generally plastic, guard 42 fits over the sharp insertion tip 26 of the longitudinal piercing member 20 and over the distal end portion 16 of a cannula 12 prior to insertion in a living subject so as to protect medical personnel from accidental injury. A butterfly 44 preferably forms a part of the catheter assembly 10. The butterfly 44 has a longitudinal opening therethrough from its proximal end 46 to its distal end 48. The cannula 12 passes through the opening in the member 44 and can be held slidingly therein so that, if desired, the cannula can be fed therethrough to a desired distance in a blood vessel. More often, however, the cannula 12 will be held non-slidingly by the member 44. The member 44 can be taped in place to provide a base for holding the catheter assembly 10, after the longitudinal piercing member 20 has been removed therefrom, in a required position relative to the body.

In accordance with the present invention, a receiving tube 50 is provided for the longitudinally piercing member 20. The receiving tube 50 has a proximal end portion 52 and a distal end portion 54. A longitudinal bore 56 extends through the receiving tube 50 from the proximal end portion 52 to the distal end portion 54. The bore 56 is designed to retain therein at least the sharp insertion tip 26 of the longitudinal piercing member 20. In instances wherein the extractor construction is an extraction wire 36 the bore 56 will usually be sufficiently long to retain the entire longitudinal piercing member 20 therein. The tube 50 is adjacent to the proximal end 32 of the hub 28 held in that position by the extraction wire 36 (FIGS. 2 and 3) or can be held in position by a fitting 57 (FIG. 4). The extraction wire 36 extends from the passageway 30 through and beyond the bore 56 of the tube 50. A knob 58 is generally attached to the proximal end of the wire 36 so that the wire 36 can be readily pulled rightwardly in FIGS. 2-4 and 6.

Note that in FIGS. 1, 2 and 3 a rubber septum 60 is attached over the proximal end 32 of the hub 28. Also note in FIGS. 1, 2 and 3 that a branch path 62 is present for introducing medicaments or the like into the passageway 30 in the hub 28. In FIG. 4 a simplier hub 28 is utilized which does not have such a branch path and, further, a septum is not present on the proximal end 32 of the hub 28. Instead, in FIG. 4 screw-on locking of the hub 28 to the distal end portion 54 of the rigid receiving tube 50 is provided. Optionally, a rubber septum 63 can be present in the distal end portion 54 of the receiving tube 50.

In accordance with certain embodiments of the present invention, a first closure 64 is located across the proximal end portion 54 of the tube 50, the first closure 64 having a generally central opening 66 which is large enough to allow the extraction wire 36 to pass longitudinally therethrough but too small to allow the longitudinal piercing member 20 to pass longitudinally therethrough. The first closure 64 can be in the nature of a polymeric plug having the central opening 66 therethrough.

Preferably the first closure 64 also includes means for holding the proximal end 22 of the longitudinally piercing member 20. In the embodiment illustrated such holding means is merely in the nature the generally central opening 66, on a bore facing end 68 thereof, being large enough for the proximal end 22 of the longitudinally piercing member 20 to enter therein in tight interference fit when the knob 58 is pulled rightwardly in FIGS. 2-4. For example, the central opening 66 can be tapered as seen best in FIG. 2A whereby the proximal end 22 of the longitudinal piercing member 20 gauges into the opening 66.

Also in accordance with certain embodiments of the present invention a second closure 70 is located across the distal end portion 54 of the receiving tube 50. The second closure 70 has a generally central access 72 through which the extraction wire 36 and the longitudinally piercing member 20 can longitudinally pass. In the embodiment of FIG. 2, the second closure 70 is in the nature of an elastomeric member or septum 74. The central access 72, in the embodiment of FIG. 2, is a self-shutting hole through the elastomeric member 74.

In the embodiment of FIG. 3, the second closure 70 is in the nature of a small passage 75 with included detents 77, the passage 75 being coaxial with the tube 50. The detents 77 serve to assure retention (entrap) of the needle or stylet 20 within the receiving tube 50 since the needle or stylet 20 must be forced past the detents 77 and such force cannot be asserted from inside the bore 56. The embodiment of FIG. 4 is like that of FIG. 3 with the exception that screw threads 76 are provided for proper mating with a flange 78 on the proximal end 72 of the hub 28.

It is important to note that in FIGS. 1-4 and 6 the proximal end 22 of the needle or stylet 20 is prevented from being withdrawn by the first closure 64 whereby the needle or stylet is retained within the receiving tube 50. Furthermore, the central access 72 through the second closure 70 is made either very small or self-sealing, or of a frictional or interference fit, whereby even if the needle or stylet 20 should work loose from the first closure 64, it will still be retained within the receiving tube 50.

FIGS. 5 and 5A show a slightly different embodiment, namely one wherein the means for holding the longitudinal piercing member 20 within the receiving tube 50 is in the nature of a spring loaded member 80 which snaps into a notch 82 in the needle or stylet 20. In the embodiment of FIGS. 5 and 5A, it is thus not necessary (but possible) that the proximal end 22 of the needle or stylet 20 be held by the first closure 64.

FIG. 5 also illustrates a structure which does not have an extraction wire 36. Instead, the extractor construction is in the nature of a proximal extension 84 of the longitudinal piercing member 22. Note that the extension 84 can pass through the first closure 64 since locking of the notch 82 in the spring loaded member 80 positively locks the longitudinal piercing member 22 in the receiving tube 50. Note also that the sharp insertion tip 26 of the longitudinal piercing member 20 is entrapped within the bore 56.

FIG. 6 illustrates an embodiment wherein the second closure 70 has a generally central access 72 which is at a non-zero angle with the axis of the receiving tube 50. The longitudinal piercing member 20 is then retained within the receiving tube 50 in the manner illustrated since the longitudinal piercing member 20 must be forced through the central access 72. Thus, the embodiment of FIG. 6, like that of FIG. 3, includes detent means associated with the access 72.

Industrial Applicability

In accordance with the present invention, an improved catheter assembly 10 is set forth wherein a needle or stylet 20 can be removed utilizing an extractor construction, for example, an extraction wire 36, and the needle or stylet 20 is automatically safely encased within a rigid receiving tube 50 thereby preventing attending medical personnel from accidentally piercing themselves or others with the sharp insertion tip 26 of the needle 20. Thus, chances are greatly reduced for transmission of such diseases as AIDS and/or hepatitis.

While the invention has been described in connection with specific embodiments thereof, it will be understood that is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. In a catheter assembly having a cannula having a proximal end portion, a distal end portion and a longitudinal duct therethrough from said proximal end portion to said distal end portion; a longitudinal piercing member having a proximal end and distal end having a sharp insertion tip, the longitudinal piercing member being positioned within the longitudinal duct of the cannula with the insertion tip extending beyond the distal end of the cannula; a hub having a passageway therethrough from the proximal end to the distal end thereof, the proximal end portion of the cannula being attached adjacent the distal end of the hub with the passageway in flow communication with the duct in the proximal end portion of the cannula; and an extraction wire having proximal and distal ends, said wire being of smaller diameter than the longitudinal piercing member, having said distal end thereof attached to extend longitudinally from the proximal end of the longitudinal piercing member, said extraction wire extending through the duct of the cannula and through the passageway of the hub to said proximal end of said wire, an improvement comprising:

a rigid longitudinal piercing member receiving tube having proximal and distal end portions and a longitudinal bore therethrough from said proximal to said distal end portion, said tube being adjacent to said proximal end of said hub, said extractor wire extending from said passageway through and beyond said bore of said tube;

a first closure across said proximal end portion of said tube, said first closure having a generally central opening large enough to allow said wire to pass longitudinally therethrough but too small to allow said longitudinal piercing member to pass fully longitudinally therethrough; and a second closure across said distal end portion of said tube, said second closure having a generally central access through which said wire and said longitudinal piercing member can longitudinally pass;

wherein said second closure includes means for automatically entrapping said insertion tip of said longitudinal piercing member in said longitudinal bore of said receiving tube, said entrapping means operating in response to said longitudinal piercing member being moved fully proximally into said receiving tube by proximal movement of said extraction wire; and wherein said second closure comprising a deformable sealing member and said central access comprises a self-sealing hole through which said longitudinal piercing member can longitudinally pass.

2. A catheter assembly as set forth in claim 1, wherein said generally central opening has a distal end and a proximal end and tapers to a smaller cross-section towards said proximal end, wherein said longitudinal piercing member is small enough to pass through said distal end but not through said proximal end of said generally central opening and becomes wedges therein.

3. A catheter assembly as set forth in claim 1, wherein said first closure about said generally central opening is of a material sufficiently softer than the material of said longitudinal piercing member so that said longitudinal piercing member can deform said generally central opening.

4. A catheter assembly as set forth in claim 1, further including:
a rubber septum covering said proximal end of said hub.

5. A catheter assembly as set forth in claim 1, wherein said deformable sealing member is elastomeric.

6. A catheter assembly as set forth in claim 1, further including:
means for attaching the distal end of the receiving tube to the proximal end of the hub.

7. A catheter assembly as set forth in claim 6, wherein said attaching means comprises an interlocking fitting.

8. In a catheter assembly having a cannula having a proximal end portion, a distal end portion and a longitudinal duct therethrough from said proximal end portion to said distal end portion; a longitudinal piercing member having a proximal end and a distal end having a sharp insertion tip, the longitudinal duct of the cannula with the insertion tip extending beyond the distal end of the cannula; a hub having a passageway therethrough from the proximal end to the distal end thereof, the proximal end portion of the cannula being attached adjacent the distal end of the hub with the passageway in flow communication with the duct in the proximal end portion of the cannula; and an extraction wire having proximal and distal ends, said wire being of smaller diameter than the longitudinal piercing member, having said distal end thereof attached to extend longitudinally from the proximal end of the longitudinal piercing member, said extraction wire extending through the duct of the cannula and through the passageway of the hub to said proximal end of said wire, an improvement comprising:

a rigid longitudinal piercing member receiving tube having proximal and distal end portions and a longitudinal bore therethrough from said proximal to said distal end portion, said tube being adjacent to said proximal end of said hub, said extractor wire extending from said passageway through and beyond said bore of said tube;

a first closure across said proximal end portion of said tube, said first closure having a generally central opening large enough to allow said wire to pass longitudinally therethrough but too small to allow said longitudinally piercing member to pass fully longitudinally therethrough;

a second closure across said distal end portion of said tube, said second closure having a generally central access through which said wire and said longitudinal piercing member can longitudinally pass;

wherein said second closure includes means for automatically entrapping said insertion tip of said longitudinal piercing member in said longitudinal bore of said receiving tube, said entrapping means operating in response to said longitudinal piercing member being moved fully proximally into said receiving tube by proximal movement of said extraction wire; and wherein said second closure comprises and elastomeric sealing member and said central access comprise a self-sealing hole through which said longitudinal piercing member can longitudinally pass.

9. A catheter assembly as set forth in claim 8, further including:
means for attaching the distal end of the receiving tube to the proximal end of the hub.

10. A catheter assembly as set forth in claim 9, wherein said attaching means comprises an interlocking fitting.

11. A catheter assembly as set forth in claim 8, further including:
a rubber septum covering said proximal end of said hub.

12. A catheter assembly as set forth in claim 9, wherein said first closure includes means for holding said proximal end of said longitudinal piercing member.

* * * * *